(12) United States Patent
Nakamura et al.

(10) Patent No.: US 6,992,197 B2
(45) Date of Patent: Jan. 31, 2006

(54) LACTONE COMPOUND

(75) Inventors: Junji Nakamura, Hiratsuka (JP); Shigetaka Numasawa, Tokyo (JP); Hiroyuki Kenmochi, Hiratsuka (JP); Yoji Hori, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 10/866,600

(22) Filed: Jun. 10, 2004

(65) Prior Publication Data
US 2005/0032887 A1 Feb. 10, 2005

(30) Foreign Application Priority Data
Jun. 12, 2003 (JP) .............................. 2003-167838

(51) Int. Cl.
*C07D 307/77* (2006.01)
(52) U.S. Cl. ..................................... 549/305
(58) Field of Classification Search ................. 549/305
See application file for complete search history.

(56) References Cited

U.S. PATENT DOCUMENTS 6,639,035 B1 * 10/2003 Chen et al. ................ 526/266
2004/0063882 A1    4/2004 Kamon et al.

FOREIGN PATENT DOCUMENTS

| EP | 1 352 904 A1 * | 10/2003 |
| JP | A-2002-234882 | 8/2002 |
| JP | A-2002-308866 | 10/2002 |

OTHER PUBLICATIONS

Urban, E. et al 'Model compounds for 'garlicin' and their antimicrobial activity in the growth-test of yeast' CA 114: 3279 (1991).*

* cited by examiner

*Primary Examiner*—Amelia A. Owens
(74) *Attorney, Agent, or Firm*—Peter F. Corless; Christine C. O'Day; Edwards & Angell, LLP

(57) ABSTRACT

A novel monomer compound having a lactone moiety of the present invention can be converted into polymers usable as resist materials with excellent properties, etc., and an alcohol compound having a lactone moiety of the invention is useful as a material for the monomer compound. The compounds are represented by the following general formula [1]:

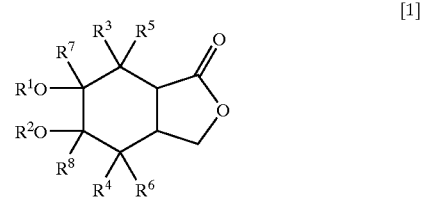

[1]

wherein one of $R^1$ and $R^2$ represents a hydrogen atom, an acryloyl group, or a methacryloyl group, and the other represents an alkyl group; $R^3$ and $R^4$ independently represent a hydrogen atom or an alkyl group; $R^5$ and $R^6$ both represent a hydrogen atom or are combined to form a methylene chain that may have an alkyl group; and $R^7$ and $R^8$ independently represent a hydrogen atom or a methyl group.

3 Claims, 10 Drawing Sheets

LACTONE COMPOUND

1. TECHNICAL FIELD

The present invention relates to a compound having a lactone moiety useful as a monomer for forming resins for paints, adhesives, binders, inks, resists, etc., and an alcohol compound having a lactone moiety useful as a material therefor.

2. BACKGROUND OF THE INVENTION

Progress has recently been made in technologies for highly integrating semiconductor devices, whereby resist materials for the devices need to have various properties including transparency, stability, hydrophobicity, heat resistance, suitable polarity, and suitable solubility in organic solvents. Compounds with a lactone moiety have been developed as the resist materials with the properties in recent years. For example, (meth)acrylate compounds with a bicyclic or tricyclic lactone moiety are proposed in JP-A-2002-234882. Further, (meth)acrylate compounds with a tricyclic lactone moiety having a substituent are proposed in JP-A-2002-308866.

3. SUMMARY OF THE INVENTION

The (meth)acrylate compounds with a lactone moiety described in JP-A-2002-234882, JP-A-2002-308866, etc. can be converted into polymers excellent in etching resistance and adhesion to substrates. However, there has been need for a monomer capable of forming a polymer having more excellent properties. Accordingly, an object of the present invention is to provide a novel monomer compound with a lactone moiety, which can be converted into polymers usable as resist materials, etc. with more excellent properties.

As a result of intense research in view of the above object, the inventors have found that a particular polycyclic compound having a lactone moiety can be used as the above monomer compound. The present invention has been accomplished by this finding.

Thus, a compound of the invention is represented by the following general formula [1]:

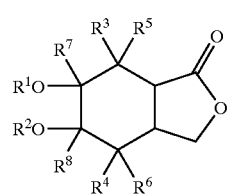

[1]

wherein one of $R^1$ and $R^2$ represents a hydrogen atom, an acryloyl group, or a methacryloyl group, and the other represents an alkyl group; $R^3$ and $R^4$ independently represent a hydrogen atom or an alkyl group; $R^5$ and $R^6$ both represent a hydrogen atom or are combined to form a methylene chain that may have an alkyl group; and $R^7$ and $R^8$ independently represent a hydrogen atom or a methyl group.

4. BRIEF DESCRIPTION OF THE DRAWINGS

5. DETAILED DESCRIPTION OF THE INVENTION

Figure 1:
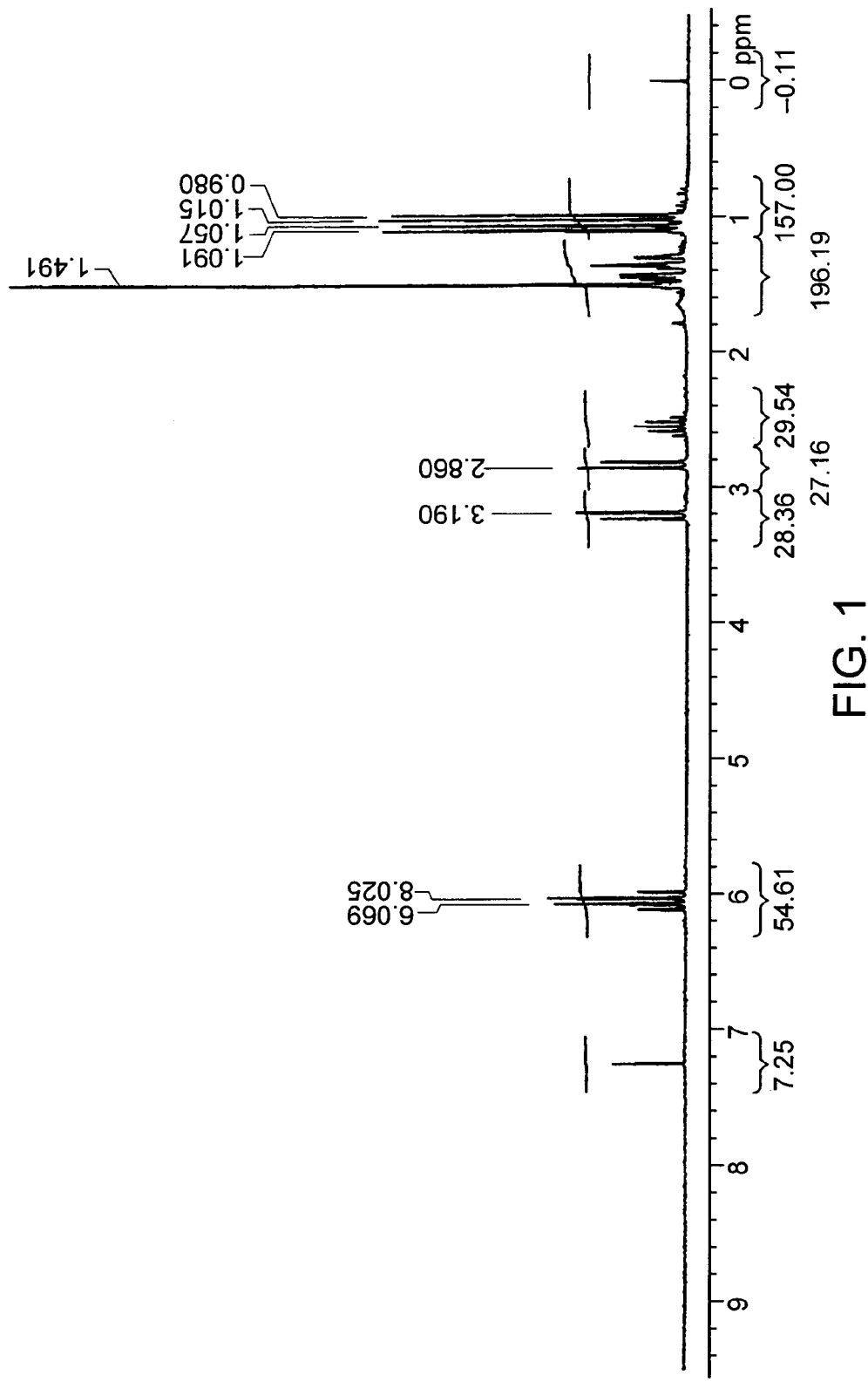
FIG. 1 is a $^1$H-NMR spectrum in chloroform-d of the product of Example 1 (1) purified by distillation.

In the compound of the present invention represented by the general formula [1], the alkyl groups represented by $R^1$ (or $R^2$), $R^3$, and $R^4$ include straight, branched, or cyclic alkyl groups having 1 to 10 carbon atoms. The carbon number of the alkyl group is preferably 1 to 8, more preferably 1 to 6. Specific examples of the alkyl groups include a methyl group, an ethyl group, a n-propyl group, an isopropyl group, a n-butyl group, a sec-butyl group, an isobutyl group, a tert-butyl group, a n-pentyl group, an isopentyl group, a tert-pentyl group, a neopentyl group, a n-hexyl group, an isohexyl group, a n-heptyl group, a n-octyl group, a 2-ethylhexyl group, a cyclopentyl group, a cyclohexyl group, a methylcyclohexyl group, etc.

Particularly preferred alkyl groups of $R^3$ and $R^4$ include a methyl group, an ethyl group, and an isopropyl group.

The methylene chain formed by $R^5$ and $R^6$ may be a methylene group, an ethylene group, a trimethylene group, etc. The methylene chain may have a substituent of an alkyl group, and examples thereof may be the same as those of $R^1$ (or $R^2$), $R^3$, and $R^4$ described above.

The compound represented by the general formula [1], in which one of $R^1$ and $R^2$ is an acryloyl group or a methacryloyl group and the other is an alkyl group, can be used as a monomer compound for forming resins for paints, bonds, adhesives, inks, resists, etc. The compound represented by the general formula [1], in which one of $R^1$ and $R^2$ is a hydrogen atom and the other is an alkyl group, is an alcohol compound having a lactone moiety usable as a starting material for the monomer compound, etc.

The compound represented by the general formula [1] includes isomers such as endo-isomers and exo-isomers.

The compound represented by the general formula [1] can be easily produced according to the following reaction scheme:

First Step

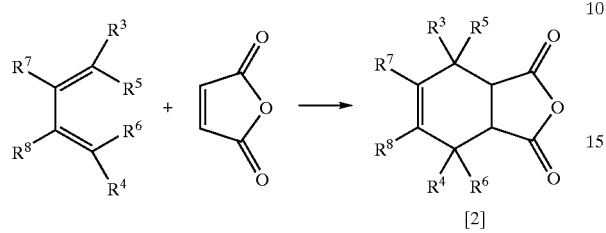

[2]

Second Step

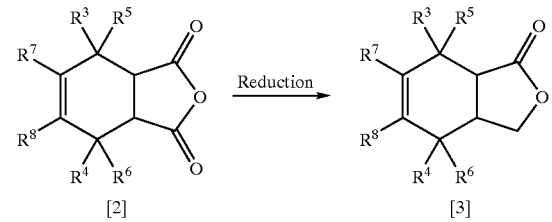

[2]　　　　　　　　　　　　　　　[3]

Third Step

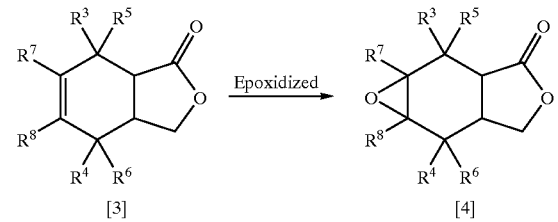

[3]　　　　　　　　　　　　　　　[4]

Fourth Step

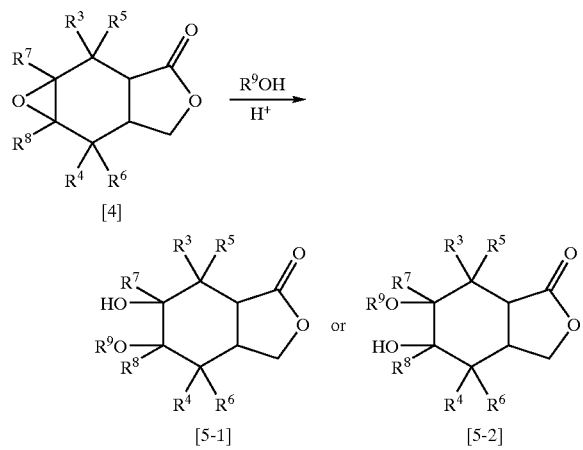

[4]

[5-1]　　　　　　　　　　　　　[5-2]

Fifth Step

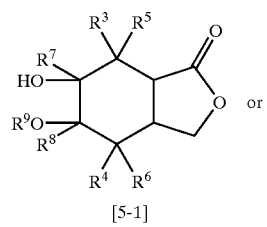

[5-1]

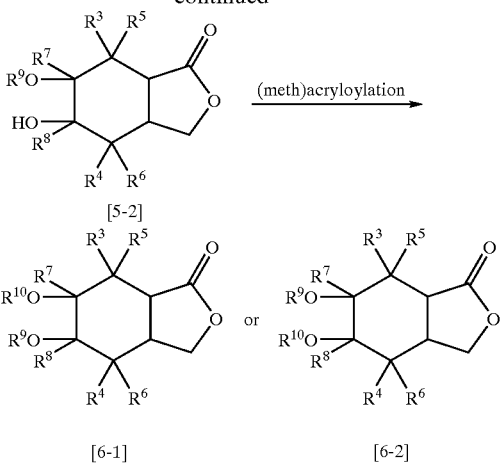

[5-2]

[6-1]　　　　　　　　　　　　　[6-2]

Thus, a cyclic olefin [2] having an acid anhydride moiety is derived as a Diels-Alder adduct from a cyclic or linear diene compound and maleic anhydride in the first step, the acid anhydride moiety is selectively reduced to generate a cyclic olefin [3] having a lactone moiety in the second step, and the cyclic olefin [3] is epoxidized to prepare an epoxy compound [4] in the third step. Then, the epoxy ring of the epoxy compound [4] is opened in the presence of an acidic substance and an alcohol $R^9OH$ (in which $R^9$ represents an alkyl group) to produce an alcohol compound having a lactone moiety [5-1] or [5-2] in the fourth step. The alcohol compounds [5-1] and [5-2] are such that one of $R^1$ and $R^2$ in the general formula [1] is a hydrogen atom and the other is an alkyl group.

The alcohol compound [5-1] or [5-2] is (meth)acryloylated with a (meth)acryloylation reagent to produce a (meth)acrylate compound [6-1] or [6-2] in the fifth step. The (meth)acrylate compounds [6-1] and [6-2] are such that one of $R^1$ and $R^2$ in the general formula [1] is an acryloyl group or a methacryloyl group and the other is an alkyl group.

The steps are described in detail below.

First Step: Diels-Alder Reaction Between Cyclic or Linear Diene Compound and Maleic Anhydride The cyclic olefin [2] having an acid anhydride moiety can be prepared by a Diels-Alder reaction between the cyclic or linear diene compound and maleic anhydride though a commercially-available compound may be used as the cyclic olefin. The Diels-Alder reaction is generally achieved by heating the starting materials in an inert solvent in a pressure-resistant sealed vessel such as an autoclave. Because maleic anhydride has remarkably high dienophilicity, the Diels-Alder reaction can be carried out at approximately 40 to 100° C. also in an open system using a reflux condenser, etc. if necessary.

The cyclic diene compound may be a conjugated diene compound having a 5- or 6-membered ring structure with 5 to 20 carbon atoms, and specific examples thereof include cyclopentadiene, 5,5-dimethylcyclopentadiene, 1,2,3,4,5-pentamethylcyclopentadiene, α-terpinene, etc. Specific examples of the linear diene compounds include 1,3-butadiene, 2,3-dimethyl-1,3-butadiene, isoprene, etc.

Thus-obtained Diels-Alder adduct [2] may be isolated or purified by a usual method such as distillation, crystallization, and chromatography.

Second Step: Selective Reduction of Acid Anhydride Moiety into Lactone Moiety

The cyclic olefin [3] having a lactone moiety can be generated by reducing the acid anhydride moiety of the cyclic olefin [2] with a metal hydride. Examples of the metal hydrides include lithium aluminum hydride, sodium borohydride, and compounds prepared by substituting part of hydrogen atoms thereof with an alcoholate, etc. The metal hydride is preferably sodium borohydride in view of handling, etc.

The amount of the metal hydride used is preferably 0.5 to 1.5 mol per 1 mol of the cyclic olefin [2].

The reduction is preferably carried out in a cyclic or acyclic ether solvent such as diethyl ether and tetrahydrofuran (hereinafter referred to as THF). The reduction temperature is −30 to 50° C., preferably 5 to 30° C. After the reduction, an acidic substance is added to neutralize or preferably acidify the reaction mixture, thereby converting the product into the lactone compound [3]. Examples of the acidic substances include mineral acids such as hydrochloric acid, sulfuric acid, and phosphoric acid, and organic acids such as acetic acid. Sulfuric acid and acetic acid are preferred from the viewpoint of handling.

Thus-obtained cyclic olefin [3] having a lactone moiety may be purified by crystallization, distillation, or chromatography.

Third Step: Epoxidation

In the third step, the cyclic olefin [3] having a lactone moiety is interacted with an epoxidation reagent such as a peroxide compound, whereby the double bond is epoxidized to prepare the epoxy compound [4].

The peroxide compound used in the epoxidation may be organic or inorganic. Examples of the organic peroxide compounds include peracetic acid, trifluoroperacetic acid, and m-chloroperbenzoic acid, and examples of the inorganic peroxide compounds include cocatalysts of hydrogen peroxide and a heteropolyacid. More preferred among them are m-chloroperbenzoic acid and the cocatalysts of hydrogen peroxide and a heteropolyacid.

Examples of solvents for the epoxidation include halogenated hydrocarbons such as methylene chloride and 1,2-dichloroethane; alcohols such as methanol, ethanol, and isopropanol; hydrocarbons such as hexane, heptane, and toluene; acetonitrile; dimethylsulfoxide; N,N-dimethylformamide; water; etc. The solvent is preferably a halogenated hydrocarbon such as methylene chloride and 1,2-dichloroethane.

The epoxidation temperature is −50 to 100° C., preferably 0 to 50° C.

Fourth Step: Epoxy Ring-opening Reaction in Presence of Acidic Substance and Alcohol The epoxy compound [4] obtained as above can be converted into the alcohol compound [5] ([5-1] or [5-2]) by opening the epoxy ring in the presence of the acidic substance and the alcohol $R^9OH$.

The acidic substance may be such a compound that can supply a hydrogen ion as a proton to the reaction system. The acidic substance may be liquid or solid, and preferably contains less water. Specific examples of the acidic substances include aliphatic carboxylic acids such as acetic acid, propionic acid, and formic acid; halogenated aliphatic carboxylic acids such as trifluoroacetic acid, trichloroacetic acid, and monochloroacetic acid; anhydrates of sulfonic acids such as methanesulfonic acid, p-toluenesulfonic acid, benzenesulfonic acid, and trifluoromethanesulfonic acid, and hydrates thereof; sulfuric acid; etc. The amount of the acidic substance is 0.01 to 2.0 parts by mol, preferably 0.05 to 0.2 parts by mol, per 1 part of the epoxy compound [4].

The alcohol $R^9OH$ for the ring-opening reaction is preferably a lower alcohol such as methanol, ethanol, n-propanol, isopropanol, n-butanol, 2-butanol, and tert-butanol. The amount of the alcohol may be 1 to 10 parts by volume per 1 part of the epoxy compound [4].

The ring-opening reaction temperature is 0 to 150° C., preferably 40 to 80° C.

Thus-obtained alcohol compound [5] ([5-1] or [5-2]) may be purified by crystallization or chromatography, or may be subjected to the next step without purification.

Fifth Step: Esterification

The alcohol compound [5] ([5-1] or [5-2]) is reacted with a (meth)acryloylation reagent such as (meth)acryloyl chloride and (meth)acrylic anhydride to achieve the esterification. The esterification is generally carried out in the presence of a base, which is preferably an organic base, particularly preferably a tertiary amine. Specific examples of the tertiary amines include aliphatic amines such as triethylamine, diisopropylethylamine, N-methylmorpholine, and N-methylpiperidine, and aromatic amines such as pyridine and α-, β-, or γ-picoline.

The amount of the base is 1.0 to 2.0 parts by mol, preferably 1.0 to 1.5 parts by mol, per 1 part of the alcohol compound [5] ([5-1] or [5-2]).

The amount of the (meth)acryloylation reagent is 1.0 to 2.0 parts by mol, preferably 1.0 to 1.5 parts by mol, per 1 part of the alcohol compound [5] ([5-1] or [5-2]).

A solvent is preferably used in the esterification. The solvent may be any solvent that has no adverse affects on the esterification. Specific examples of preferable solvents include aromatic hydrocarbons such as toluene and xylene, and cyclic or acyclic ethers such as THF and dimethoxyethane.

Further, the esterification efficiency may be increased by adding a compound such as 4-dimethylaminopyridine to the reaction mixture, if necessary.

The esterification temperature may be −20 to 100° C., preferably 0 to 60° C.

A polymerization inhibitor is preferably used to prevent polymerization of the ester compound during aftertreatments and purification. Examples of the polymerization inhibitors include phenol-based compounds such as hydroquinone and 4-methoxyphenol, and N-oxyl compounds such as 4-hydroxy-2,2,6,6-tetramethylpiperidine-N-oxyl.

Specific examples of the compounds of the invention wherein in the general formula [1] one of $R^1$ and $R^2$ is an acryloyl group or a methacryloyl group and the other is an alkyl group as obtained in the above manner are illustrated below.

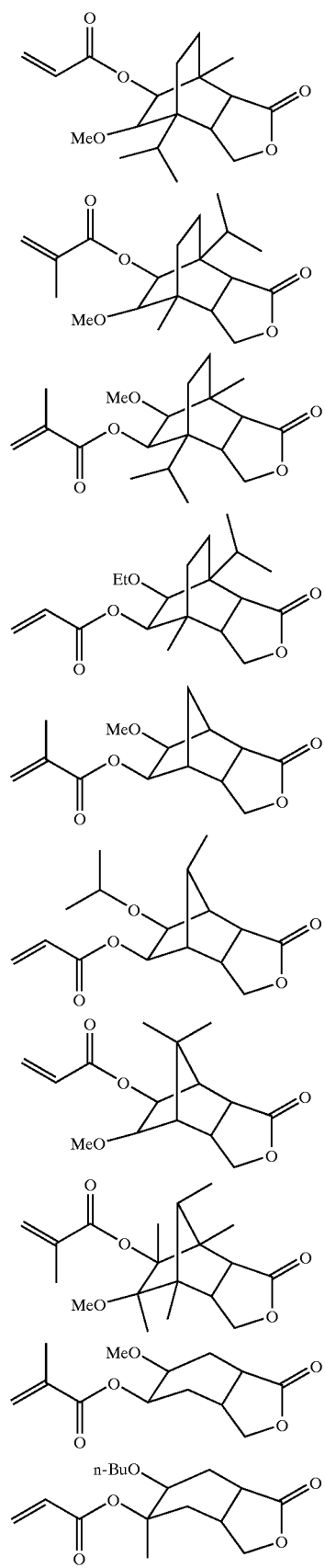
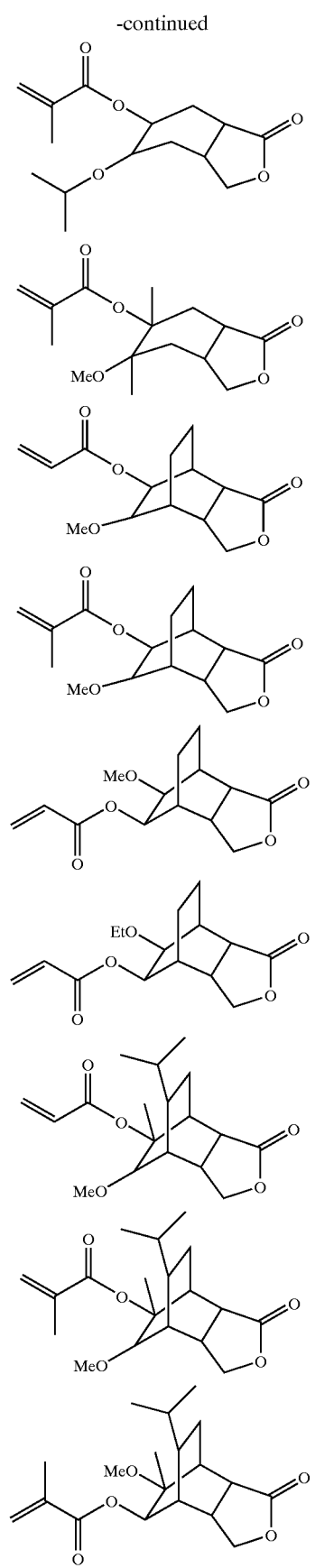

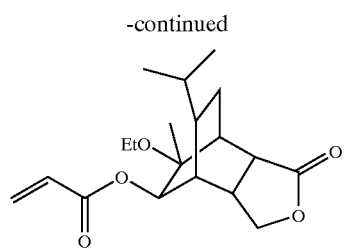
Further, specific examples of the alcohol compounds of the invention wherein in the general formula [1] one of $R^1$ and $R^2$ is a hydrogen atom and the other is an alkyl group are illustrated below.
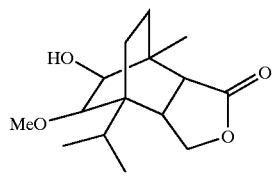
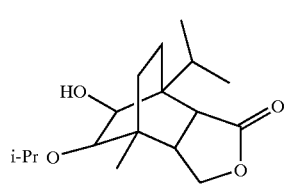
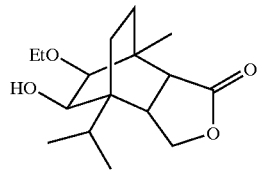
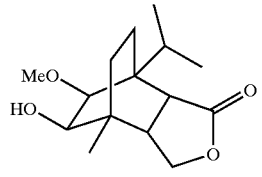
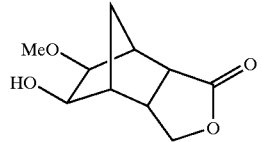
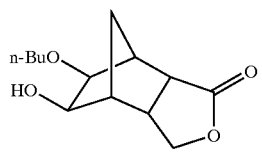
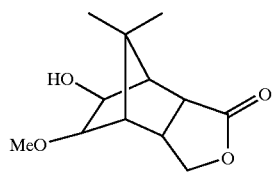
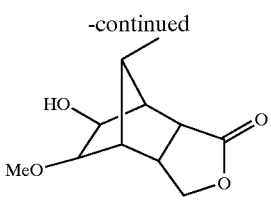
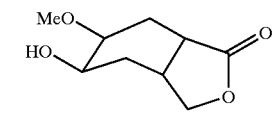
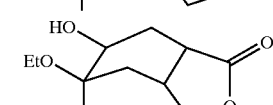
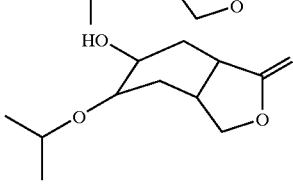
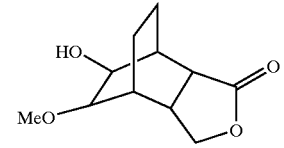
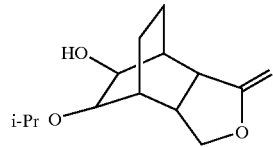
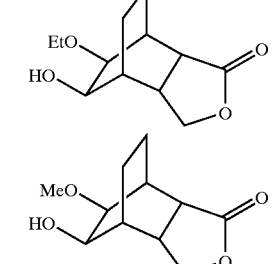
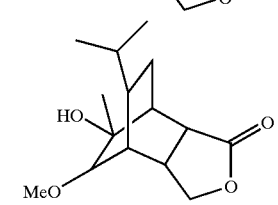
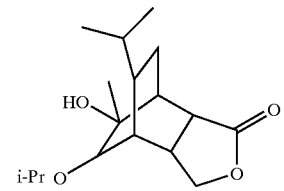

-continued

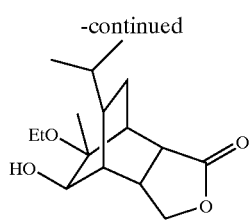

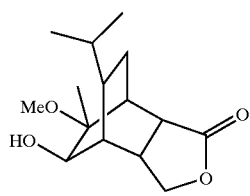

In production of the compounds of the invention, various isomers including exo isomers and endo isomers having different configurations are generated in the Diels-Alder addition reaction. The alcohol compounds and the (meth) acryloylated compounds of the invention are obtained as mixtures of the isomers. Though the isomers maybe isolated by chromatography, etc. if necessary, the mixture can be used as a monomer for forming polymers usable as base resins of resist materials, etc. without isolation.

The compound of the invention wherein in the general formula [1] one of $R^1$ and $R^2$ is an acryloyl group or a methacryloyl group and the other is an alkyl group is a (meth)acrylate compound having a lactone moiety and an alkoxy group in the same molecule. The (meth)acrylate compound has heat resistance and suitable polarity because of the structure, and can show various effects due to the alkoxy group.

In particular, the (meth)acrylate compound of the invention has an alkoxy group at the 8- or 9-position in the general formula [1] to show high polarity, high hydrophilicity, and excellent solubility in organic solvents, so that the (meth) acrylate compound is more suitable for producing (co) polymers by solution polymerization than the same type of conventional compounds having a hydrogen atom or an alkyl group at the position. Further, also polymers obtained by polymerizing the (meth)acrylate compound have excellent solvent-solubility because of the alkoxy group at the 8- or 9-position.

Resist materials using the polymers as base resins are suitable for microfabrication using far ultraviolet rays such as ArF excimer laser and KrF excimer laser, electron beams, etc., and can form a highly fine pattern in production of semiconductors.

Further, the (meth)acrylate compound of the invention has a boiling point lower than those of the same type of conventional compounds, and thereby can be easily purified by distillation, etc. and can be easily used as a monomer for polymerization advantageously in comparison with the same type of conventional compound.

The alcohol compound of the invention wherein in the general formula [1] one of $R^1$ and $R^2$ is a hydrogen atom and the other is an alkyl group can be used as a material for the (meth)acrylate compound with an acryloyl group or a methacryloyl group of $R^1$ or $R^2$.

EXAMPLES

The present invention will be described in more detail below with reference to Examples without intention of restricting the scope of the invention.

$^1$H-NMR spectra were measured by Varian GEMINI 2000 instrument or Bruker DRX-500 instrument using an internal standard substance of tetramethylsilane.

Example 1

Synthesis of mixture of 8-methacryloyloxy-9-methoxy-7-isopropyl-1-methyl-4-oxatricyclo[5,2,2,0$^{2,6}$] dodecan-3-one, 8-methacryloyloxy-9-methoxy-1-isopropyl-7-methyl-4-oxatricyclo[5,2,2,0$^{2,6}$] dodecan-3-one, 8-methoxy-9-methacryloyloxy-7-isopropyl-1-methyl-4-oxatricyclo[5,2,2,0$^{2,6}$] dodecan-3-one, and 8-methoxy-9-methacryloyloxy-1-isopropyl-7-methyl-4-oxatricyclo[5,2,2,0$^{2,6}$] dodecan-3-one (1) Synthesis of mixture of 7-isopropyl-1-methyl-4-oxatricyclo[5,2,2,0$^{2,6}$]-8-dodecen-3,5-dione and 1-isopropyl-7-methyl-4-oxatricyclo[5,2,2,0$^{2,6}$]-8-dodecen-3,5-dione

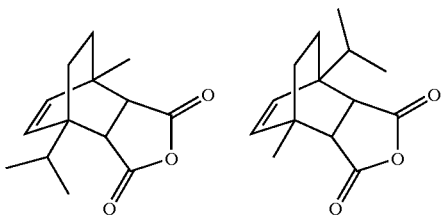

98 g (1.0 mol) of maleic anhydride and 200 mL of toluene were added to a 1000-mL flask, and stirred to dissolve maleic anhydride. 186 g of α-terpinene (purity 87%, α-terpinene content 163 g, 1.2 equivalents based on maleic anhydride) was added to the resulting solution at 60° C., and stirred at 80° C. for 2 hours. After the reaction, toluene and α-terpinene were distilled under reduced pressure to obtain 248 g of a crude product with a purity of 96%. The crude product yield was 106%. The crude product (hereinafter referred to as a crude DA adduct) was directly used in the next step.

In addition, the crude product was distilled under conditions of 128° C. and 26.7 Pa to obtain a purified product.

A $^1$H-NMR spectrum in chloroform-d of the distilled, purified product is shown in FIG. 1.

(2) Synthesis of mixture of 7-isopropyl-1-methyl-4-oxatricyclo[5,2,2,0$^{2,6}$]-8-dodecen-3-one and 1-isopropyl-7-methyl-4-oxatricyclo[5,2,2,0$^{2,6}$]-8-dodecen-3-one

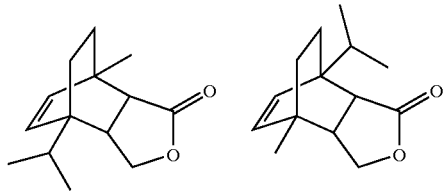

Under nitrogen atmosphere, 13.64 g (0.36 mol) of sodium borohydride and 270 mL of THF were added to a 1000-mL reaction vessel, and 0.8 mL of methanol was further added thereto. A solution of 100 g (0.41 mol) of the crude DA adduct obtained in the above step (1) and 180 mL of THF were added to the resultant mixture dropwise while cooling them by an ice bath to keep the reaction temperature at 20° C. or lower. Then, the ice bath was removed, the reaction mixture was stirred at room temperature for 8 hours, the reaction was quenched by addition of an aqueous 50-weight-% acetic acid solution, and THF was recovered. Toluene and water were added to the resultant mixture, the organic layer was separated, and toluene was distilled from the organic layer to obtain 100 g of a crude product with a purity of 90%. Further, the crude product was purified by distillation under conditions of 120° C. and 26.7 Pa to obtain 65 g of a desired product (72% yield).

Figure 2:
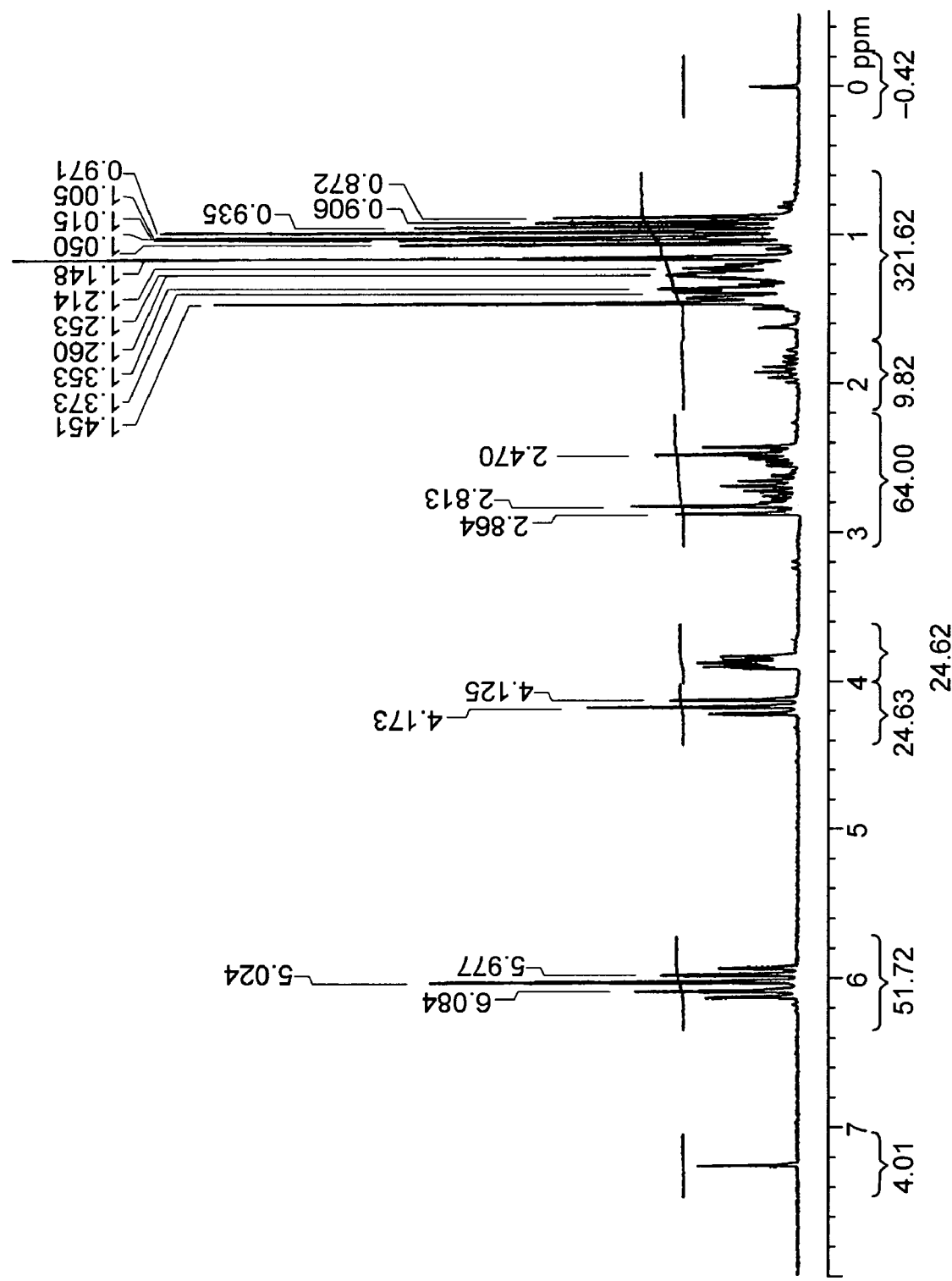
FIG. 2 is a $^1$H-NMR spectrum in chloroform-d of the product of Example 1 (2) purified by distillation.

A $^1$H-NMR spectrum in chloroform-d of the distilled, purified product is shown in FIG. 2.

(3) Synthesis of mixture of 8,9-epoxy-7-isopropyl-1-methyl-4-oxatricyclo[5,2,2,0$^{2,6}$]dodecan-3-one and 8,9-epoxy-1-isopropyl-7-methyl-4-oxatricyclo[5,2,2,0$^{2,6}$]dodecan-3-one

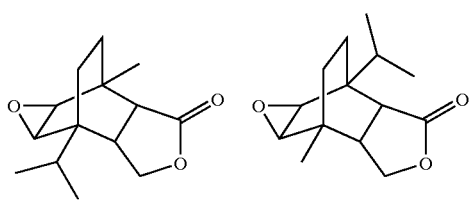

150 g (0.68 mol) of the mixture obtained in the above step (2) and 200 mL of CH$_2$Cl$_2$ were added to a 2000-mL flask, and stirred to dissolve the mixture. A solution of 176.3 g (1.02 mol) of m-chloroperbenzoic acid and 1200 mL of CH$_2$Cl$_2$ was added to the resultant solution dropwise, and stirred at 30° C. for 2 days. After the reaction, 400 g of an aqueous 20% sodium sulfite solution was added to the resultant. Then, an iodine check sheet was used to detect peroxides in the resultant liquid, and as a result, no peroxides were detected. A solution prepared by dissolving 200 g of sodium hydrogen carbonate in 1000 mL of water was added to the liquid, and stirred for a while. The aqueous layer was removed, and the organic layer was concentrated, whereby 227 g of a crude product with a purity of 85% was obtained. The crude product was directly used in the next step.

The crude product can be purified by crystallization if necessary.

Figure 3:
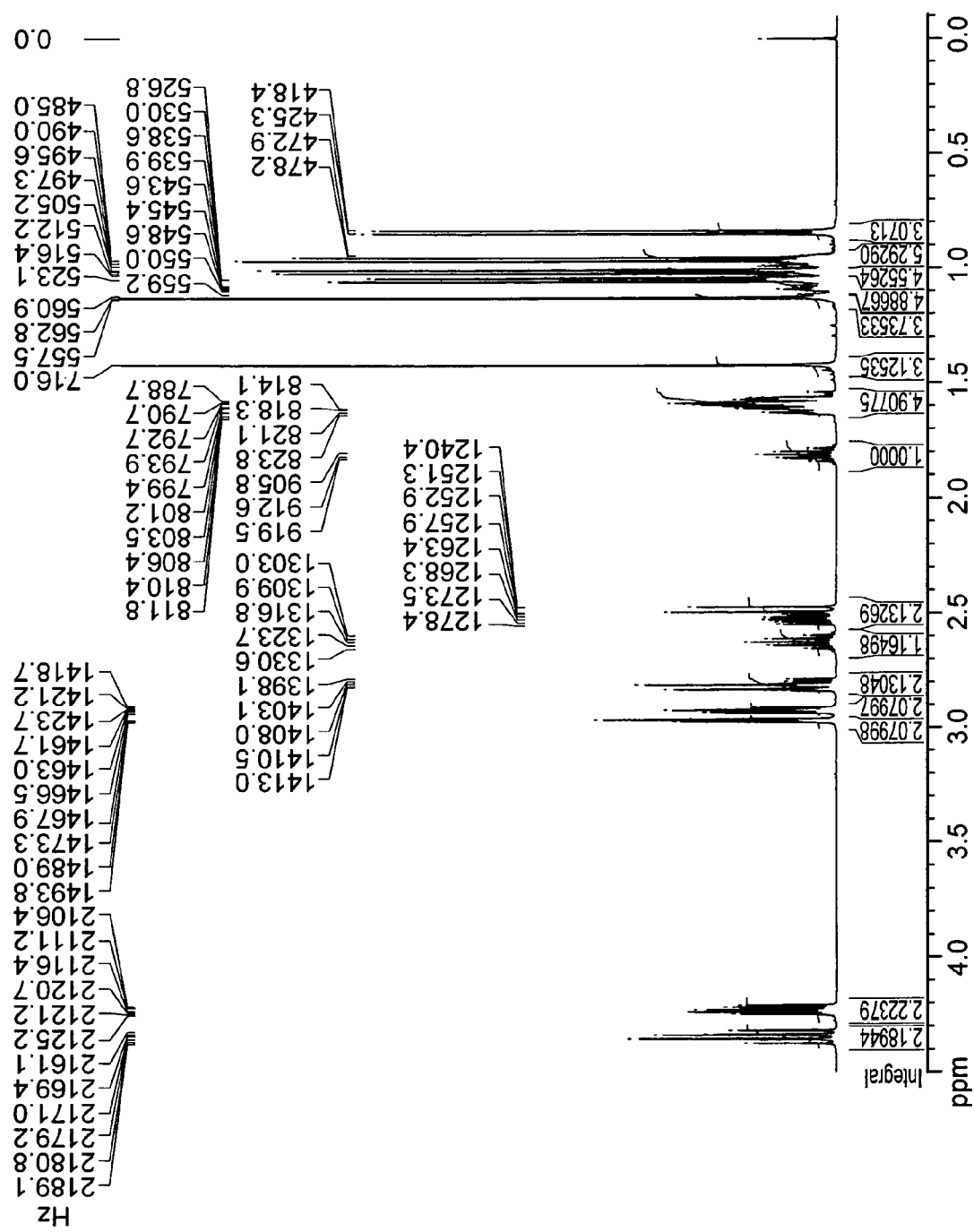
FIG. 3 is a $^1$H-NMR spectrum in chloroform-d of the product of Example 1 (3) purified by crystallization (numerals written below the spectrum indicate the integral value)
Figure 4:
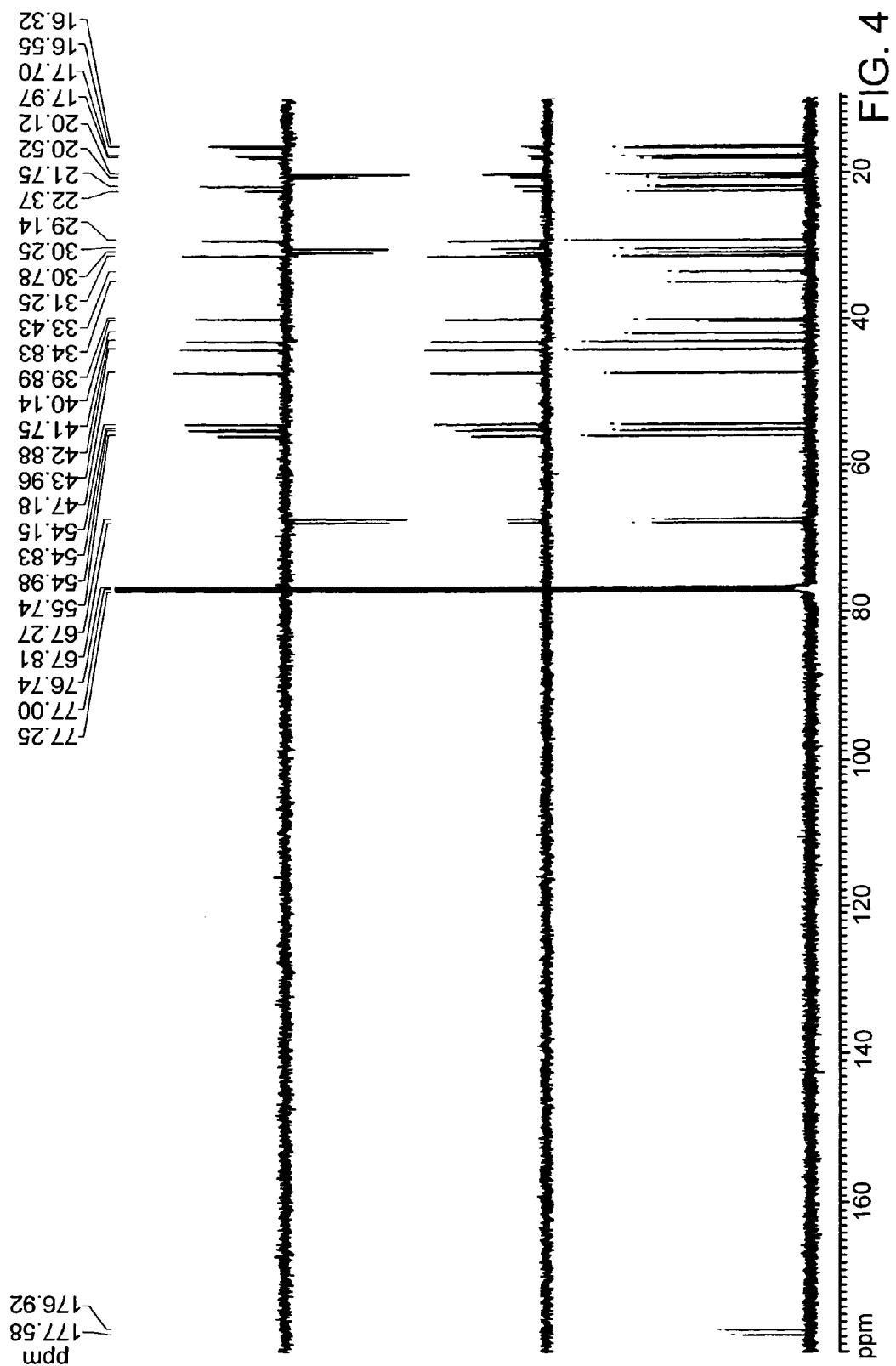
FIG. 4 is a $^{13}$C-NMR spectrum of the product of Example 1 (3) purified by crystallization.

A $^1$H-NMR spectrum in chloroform-d of the product purified by crystallization is shown in FIG. 3. Further, a $^{13}$C-NMR spectrum of the product is shown in FIG. 4.

(4) Synthesis of mixture of 8-hydroxy-9-methoxy-7-isopropyl-1-methyl-4-oxatricyclo[5,2,2,0$^{2,6}$]dodecan-3-one, 8-hydroxy-9-methoxy-1-isopropyl-7-methyl-4-oxatricyclo[5,2,2,0$^{2,6}$]dodecan-3-one, 8-methoxy-9-hydroxy-7-isopropyl-1-methyl-4-oxatricyclo[5,2,2,0$^{2,6}$]dodecan-3-one, and 8-methoxy-9-hydroxy-1-isopropyl-7-methyl-4-oxatricyclo[5,2,2,0$^{2,6}$]dodecan-3-one

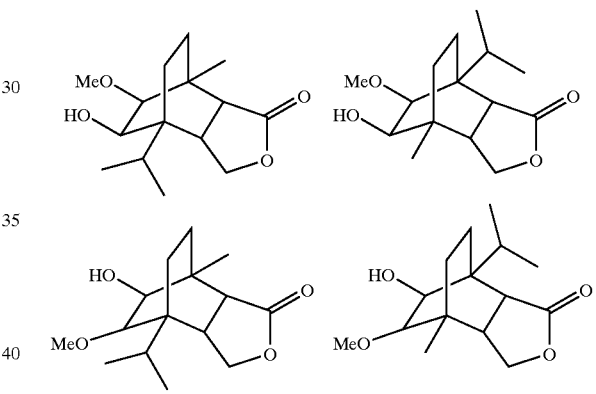

Under nitrogen atmosphere, 176 g (0.62 mol) of the mixture obtained in the above step (3) and 875 g of methanol were added to a 3000-mL flask, and stirred to dissolve the epoxy compound.

14.2 g (0.07 mol) of p-toluenesulfonic acid monohydrate was added to the resultant solution, and refluxed for 2 days while heating. After the reaction, the resulting mixture was concentrated, and toluene and water were added to the residue and stirred. The toluene layer was isolated, and water was removed from the toluene layer by azeotropic distillation, to obtain 1041 g of a toluene solution of a crude product. The crude solution was directly used in the next step.

The crude product can be further purified by crystallization if necessary.

Figure 5:
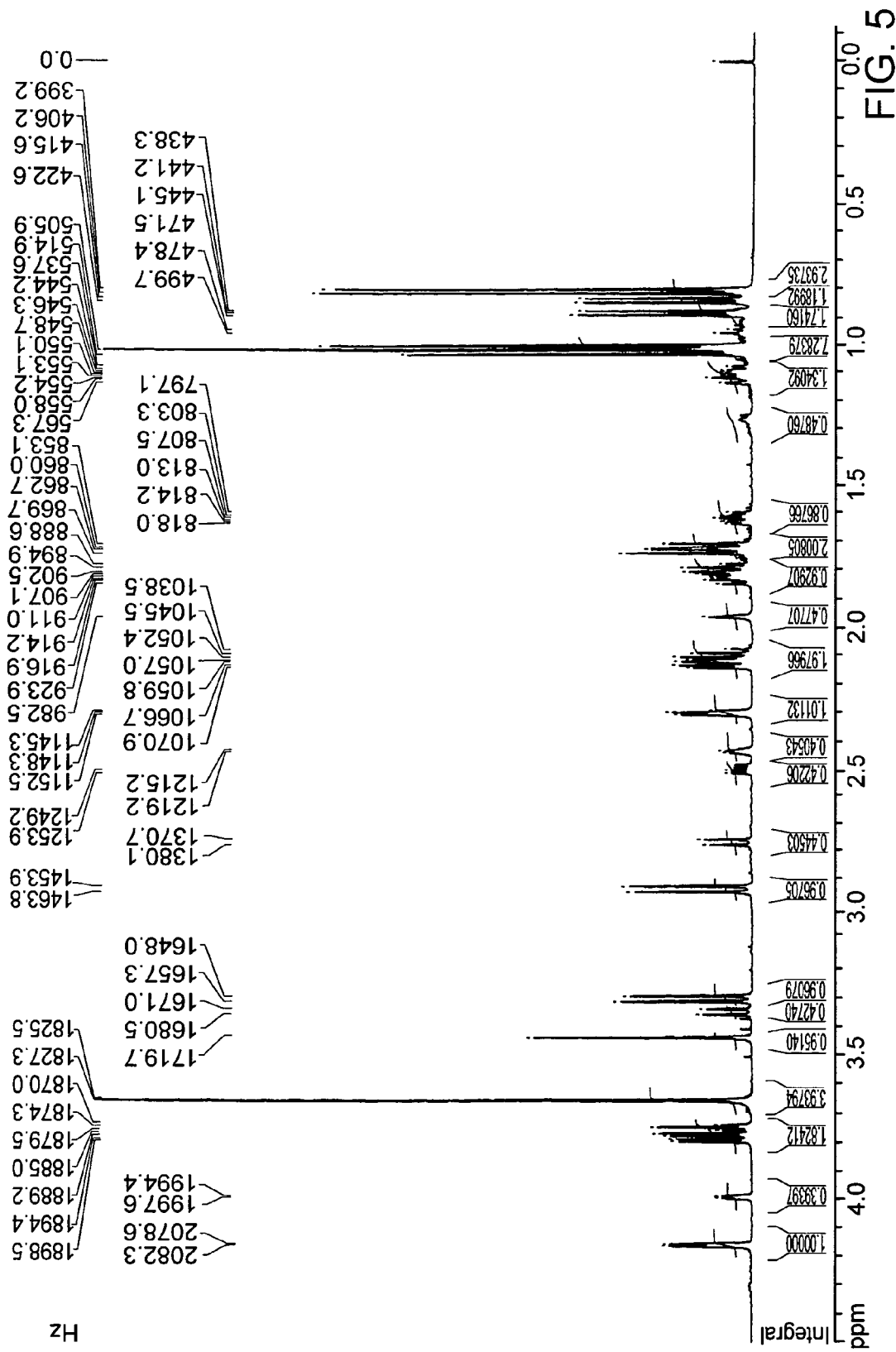
FIG. 5 is a $^1$H-NMR spectrum in chloroform-d of the product of Example 1 (4) purified by crystallization (numerals written below the spectrum indicate the integral value)
Figure 6:
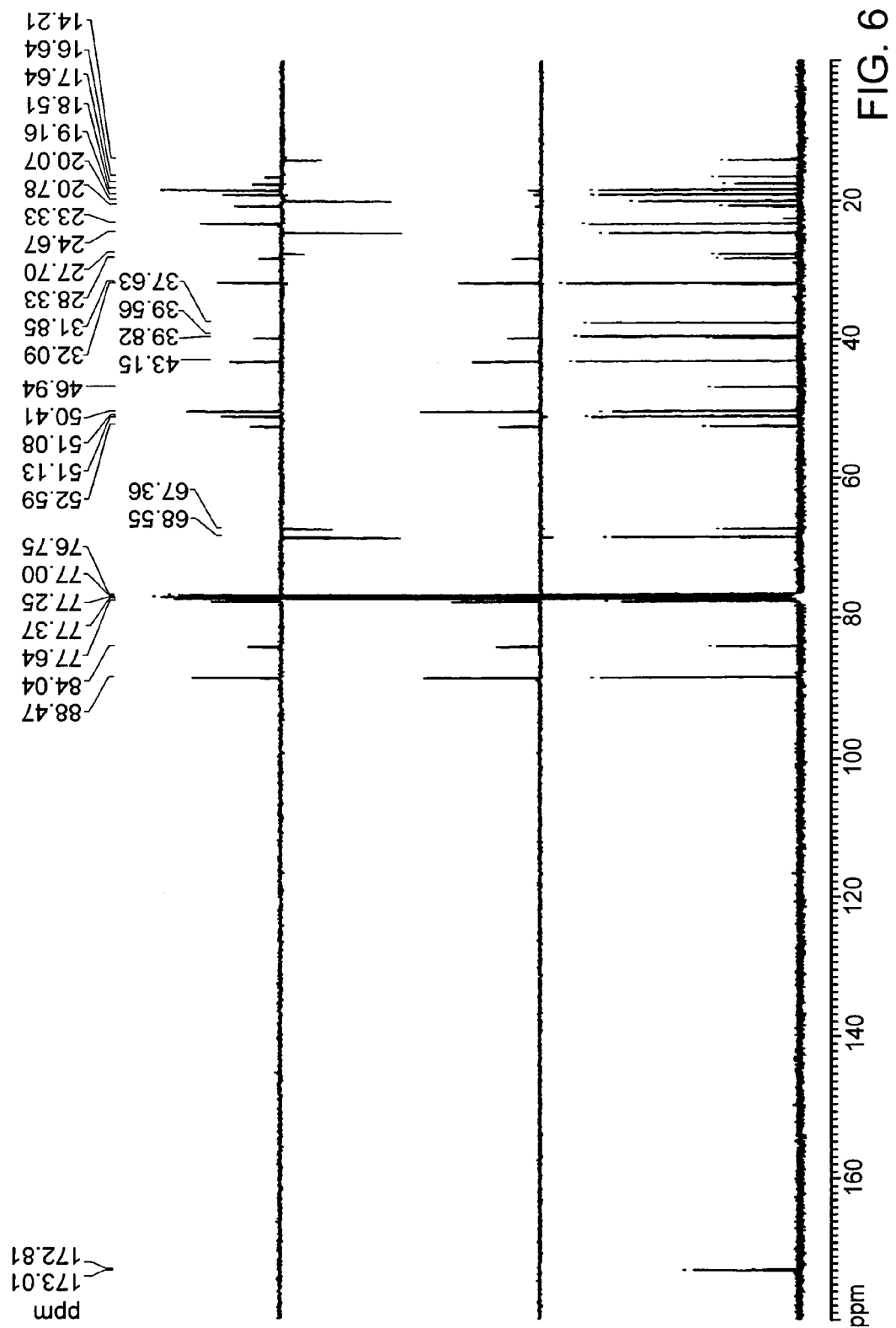
FIG. 6 is a $^{13}$C-NMR spectrum of the product of Example 1 (4) purified by crystallization.

A $^1$H-NMR spectrum in chloroform-d of the product purified by crystallization is shown in FIG. 5. Further, a $^{13}$C-NMR spectrum of the product is shown in FIG. 6.

The NMR spectra support that the obtained product is a mixture containing 4 alcohol isomers.

(5) Synthesis of mixture of 8-methacryloyloxy-9-methoxy-7-isopropyl-1-methyl-4-oxatricyclo [5,2,2,0$^{2,6}$]dodecan-3-one, 8-methacryloyloxy-9-methoxy-1-isopropyl-7-methyl-4-oxatricyclo [5,2,2,0$^{2,6}$]dodecan-3-one, 8-methoxy-9-methacryloyloxy-7-isopropyl-1-methyl-4-oxatricyclo[5,2,2,0$^{2,6}$]dodecan-3-one, and 8-methoxy-9-methacryloyloxy-1-isopropyl-7-methyl-4-oxatricyclo[5,2,2,0$^{2,6}$]dodecan-3-one

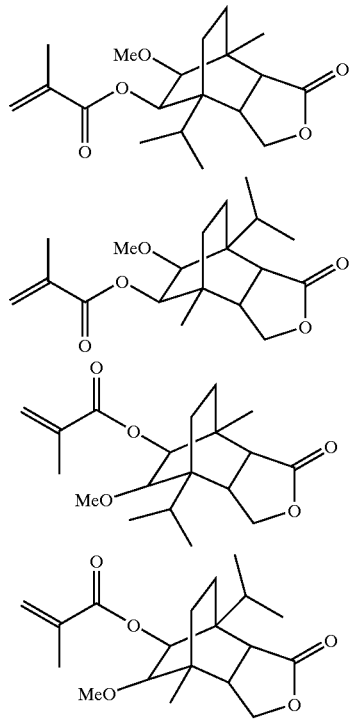

Under nitrogen atmosphere, 4.3 g of 4-dimethylaminopyridine and 990 g of the toluene solution containing 157.5 g (0.587 mol) of the isomers obtained in the above step (4) were added to a 2000-mL flask. To the solution was added 277 g of a toluene solution containing 153 g (0.993 mol) of methacrylic anhydride while cooling the solution by an ice bath, and 122 g of triethylamine was added thereto dropwise. After the addition, the resultant mixture was stirred at room temperature for 2 hours, and further stirred at 40° C. for 2 hours, and 15.9 g of methanol was added to the mixture to stop the reaction. Then, 615 mL of an aqueous 10% sulfuric acid solution was added to the mixture and stirred for 10 minutes, and the organic layer was separated. The organic layer was washed with 1000 g of an aqueous 10% potassium carbonate solution, and further washed with 1000 mL of water three times. Then, an N-oxyl compound as a polymerization inhibitor was added to the organic layer, toluene was removed under reduced pressure, and the residue was distilled under conditions of 146 to 148° C. and 20.0 Pa, to obtain 109.3 g of the desired product (51% yield).

Figure 7:
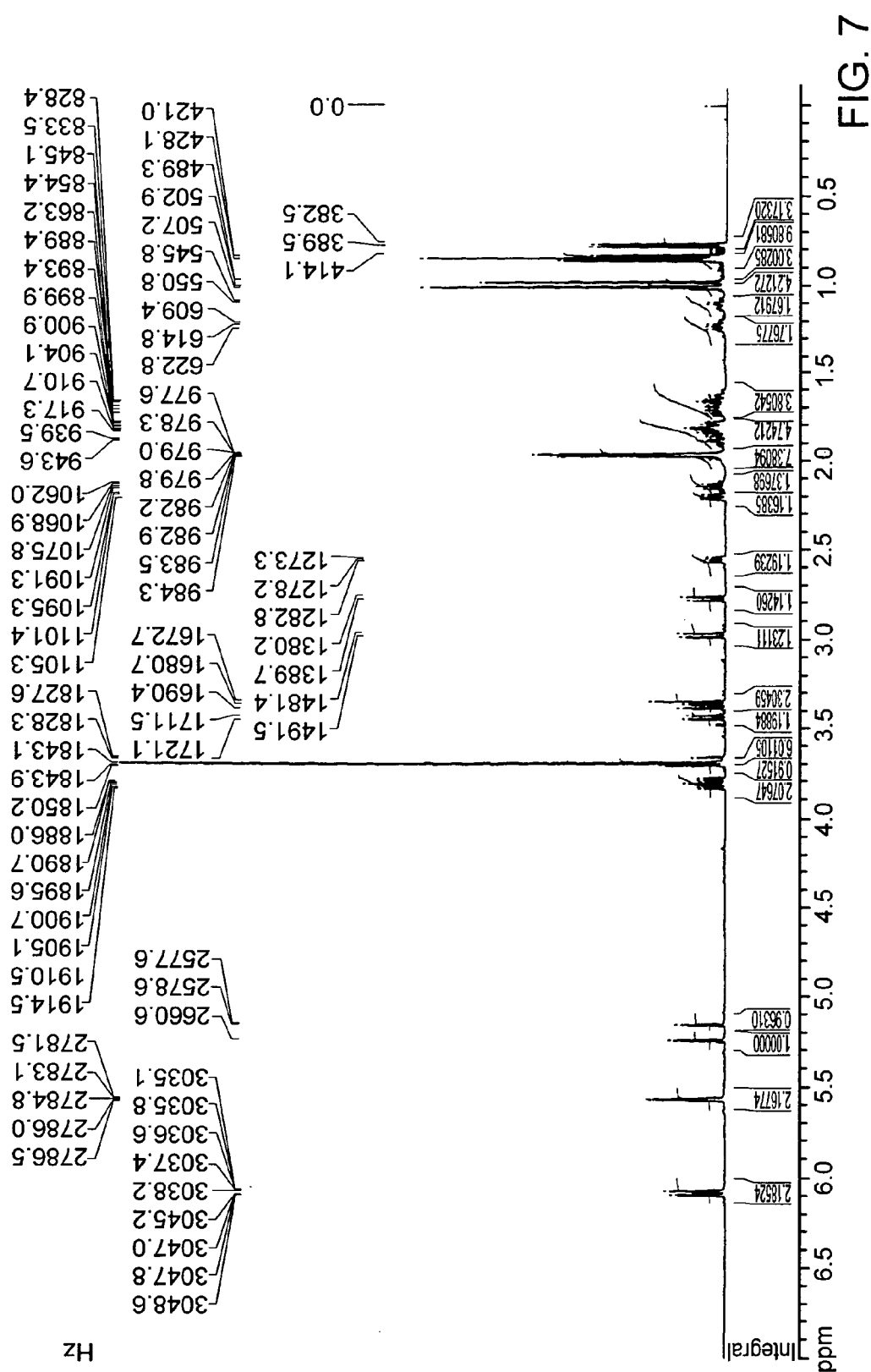
FIG. 7 is a $^1$H-NMR spectrum in chloroform-d of the product of Example 1 (5) purified by distillation (numerals written below the spectrum indicate the integral value)
Figure 8:
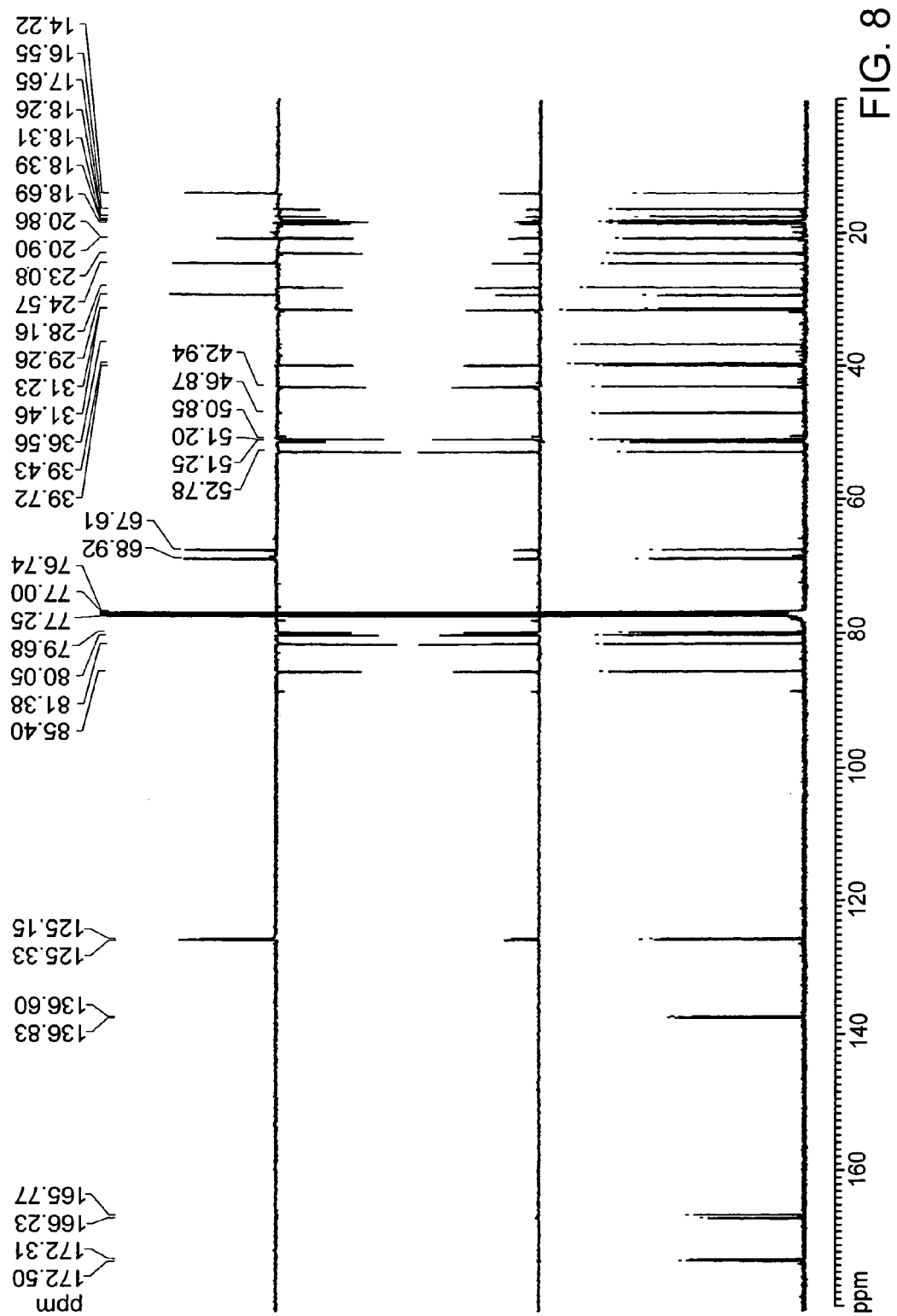
FIG. 8 is a $^{13}$C-NMR spectrum of the product of Example 1 (5) purified by distillation

A $^1$H-NMR spectrum in chloroform-d of the distilled, purified product is shown in FIG. 7. Further, a $^{13}$C-NMR spectrum of the product is shown in FIG. 8.

The NMR spectra support that the obtained product is a mixture containing 4 ester isomers.

Example 2

Synthesis of mixture of 8-methacryloyloxy-9-methoxy-4-oxatricyclo[5,2,1,0$^{2,6}$]decan-3-one and 8-methoxy-9-methacryloyloxy-4-oxatricyclo[5,2,1,0$^{2,6}$]decan-3-one (1) Synthesis of 4-oxatricyclo[5,2,1,0$^{2,6}$]decan-3-one

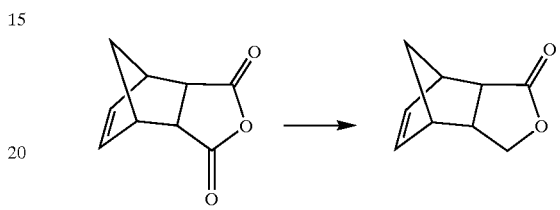

Under nitrogen atmosphere, 176 g (4.649 mol) of sodium borohydride was put into a flask and 2000 g of THF and 9.8 g of methanol were added thereto. A solution of 954 g (5.812 mol) of 5-norbornene-2,3-dicarboxylic anhydride dissolved in 2800 g of THF was added thereto dropwise while cooling them by an ice bath to keep the reaction temperature at 35° C. or lower. After completion of the dropping, the mixture was stirred at 30° C. for 4 hours, then poured into 3000 g of 10% aqueous sulfuric acid solution at 20° C. or lower and stirred for a while. Under reduced pressure, THF was recovered, and 1800 g of MIBK was added thereto for extraction. Further 900 g of MIBK was added to the separated aqueous layer for extraction and combined with the organic layer. 63.6 g of sodium carbonate and 200 g of water were added to the organic layer and stirred for a while. The separated organic layer was washed with diluted sulfuric acid and water, then concentrated, thereby 565.3 g of a white solid desired product of a lactone compound was obtained (64.76% yield).

(2) Synthesis of 8,9-epoxy-4-oxatricyclo[5,2,1,0$^{2,6}$]decan-3-one

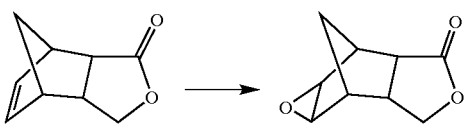

640 g (4.265 mol) of the lactone compound obtained in the above step (1), 28.14 g (2 mol %) of NaWO$_4$.2H$_2$O, 17.24 g (1 mol %) of {(Oct)$_3$MeN}Cl, 4.92 g (1 mol %) of 85% H$_3$PO$_4$, 29.44 g (5 mol %) of NaHSO$_4$.H$_2$O and 640 g of toluene were put into a flask and stirred for a while in an ice bath. Then 725 g (1.5 eq) of 30% H$_2$O$_2$ was added thereto dropwise while keeping the reaction temperature at 30° C. or lower. After completion of the dropping, the mixture was stirred at 50° C. for 1 day, then 2240 g of toluene was added thereto and the mixture was cooled. A solution of 600 g of sodium sulfite dissolved in 3250 g of water was added to the resultant solution dropwise while keeping the temperature at 20° C. or lower. After the organic layer was separated, it was washed with water twice. Then the organic layer was concentrated, thereby 381 g of a white solid desired product of an epoxy compound was obtained (53.76% yield).

(3) Synthesis of mixture of 8-hydroxy-9-methoxy-4-oxatricyclo[5,2,1,0$^{2,6}$]decan-3-one and 8-methoxy-9-hydroxy-4-oxatricyclo[5,2,1,0$^{2,6}$]decan-3-one

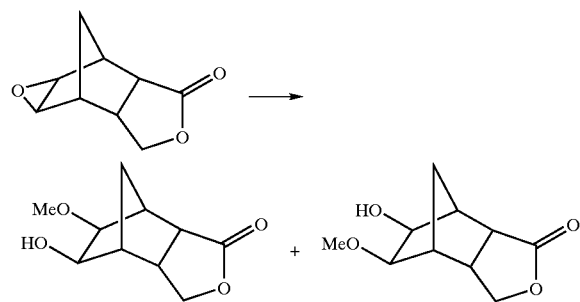

After 370 g (2.226 mol) of the epoxy compound obtained in the above step (2) was dissolved in 740 g of toluene and 1850 g of methanol, 21.82 g (0.222 mol) of methanesulfonic acid was added thereto and stirred at 50° C. for 2 days. After the solvent was recovered and made a toluene solution, it was neutralized with aqueous sodium carbonate solution. Then the resultant salt was removed by filtration. After water was removed by toluene azeotropic distillation, a desired product of a hydroxy compound was used in the next step as having a 100% yield.

(4) Synthesis of mixture of 8-methacryloyloxy-9-methoxy-4-oxatricyclo[5,2,1,0$^{2,6}$]decan-3-one and 8-methoxy-9-methacryloyloxy-4-oxatricyclo[5,2,1,0$^{2,6}$]decan-3-one

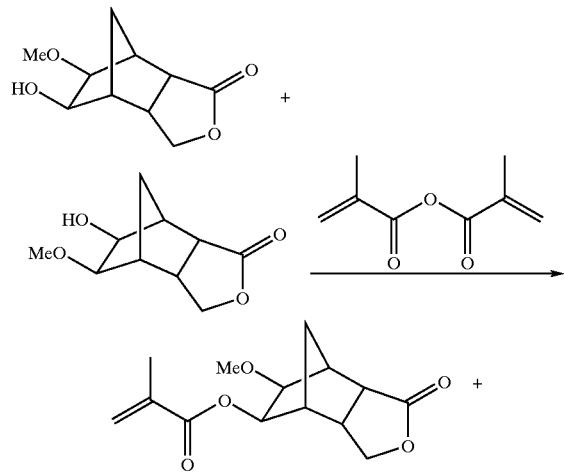

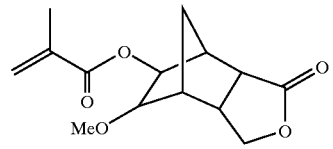

4-dimethylaminopyridine (0.111 mol) was added to 2443 g of toluene solution containing 445 g (2.226 mol) of the hydroxy compound obtained in the above step (3), then 363.3 g (2.365 mol) of methacrylic anhydride was added therto dropwise at room temperature. Further, 227.0 g (2.468 mol) of triethylamine was added thereto dropwise at room temperature, stirred for 10 hours. Then, 71.9 g of methanol was added thereto, cooled to 10° C. or lower, and 1250 g of 10% aqueous sulfuric acid solution was added thereto. After the mixture was stirred for a while, the organic layer was separated and washed with water. 900 g of 20% aqueous potassium carbonate solution was added to the organic layer for washing, and the organic layer was further washed with water. Then the organic layer was concentrated, thereby 386 g of a brown solution of a crude product was obtained.

336 g of the crude product was distilled under reduced pressure (103 to 105° C. and 26.7 Pa), thereby 283 g (1.044 mol) of the desired product with a GC purity of 98% was obtained (46.89% yield).

Figure 9:
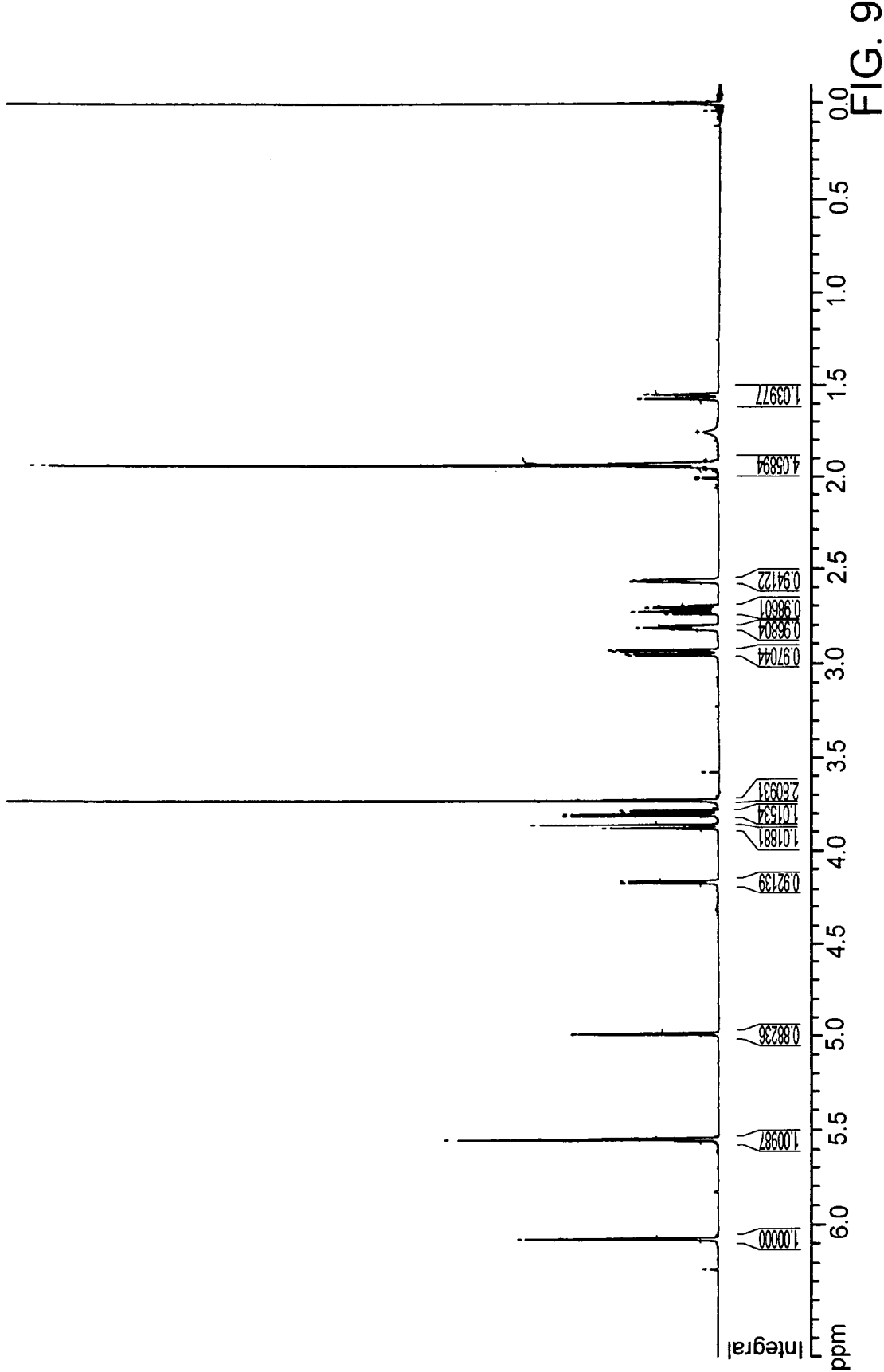
FIG. 9 is a $^1$H-NMR spectrum in chloroform-d of the product of Example 2 (4) purified by crystallization (numerals written below the spectrum indicate the integral value)
Figure 10:
FIG. 10 is a $^{13}$C-NMR spectrum in chloroform-d of the product of Example 2 (4) purified by crystallization.

A $^1$H-NMR spectrum in chloroform-d of the distilled, purified product is shown in FIG. 9. Further, a $^{13}$C-NMR spectrum of the product is shown in FIG. 10.

The (meth)acrylate compound having a lactone moiety of the present invention can be used as a monomer compound for forming polymers usable as resist materials with excellent properties, etc., and the alcohol compound having a lactone moiety of the invention is useful as a material for the monomer compound, etc. The monomer compound of the invention has the following excellent properties.

i) The monomer compound shows heat resistance and suitable polarity, and has an alkoxy group at the 8- or 9-position in the general formula [1] to show high polarity, high hydrophilicity, and excellent solubility in organic solvents, so that the monomer compound is more useful for producing (co)polymers by solution polymerization than the same type of conventional compounds having a hydrogen atom or an alkyl group at the position.

ii) Also (co)polymers obtained by (co)polymerizing the monomer compound of the invention have excellent solvent-solubility because of the alkoxy group at the 8- or 9-position.

iii) Resist materials using the (co)polymers obtained by (co)polymerizing the monomer compound of the invention as base resins are suitable for microfabrication using far ultraviolet rays such as ArF excimer laser and KrF excimer laser, electron beams, etc., and can form a highly fine pattern in production of semiconductors.

iv) The monomer compound of the invention has a boiling point lower than those of the same type of conventional compounds, and thereby can be easily purified by distillation, etc. and can be easily used for polymerization advantageously in comparison with the same type of conventional compounds.

What is claimed is:

1. A compound represented by the following general formula [1]:

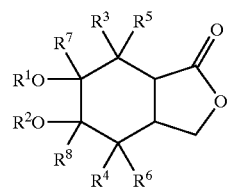

[1]

wherein one of $R^1$ and $R^2$ represents a hydrogen atom, an acryloyl group, or a methacryloyl group, and the other represents an alkyl group; $R^3$ and $R^4$ represent an alkyl group; $R^5$ and $R^6$ both represent a hydrogen atom or are combined to form a methylene chain that may have an alkyl group; and $R^7$ and $R^8$ independently represent a hydrogen atom or a methyl group.

2. The compound according to claim 1, wherein one of $R^1$ and $R^2$ in the general formula [1] represents an acryloyl group or a methacryloyl group, and the other represents an alkyl group.

3. The compound according to claim 1, wherein one of $R^1$ and $R^2$ in the general formula [1] represents a hydrogen atom, and the other represents an alkyl group.

* * * * *